United States Patent
Mendrok-Edinger

(10) Patent No.: US 10,933,002 B2
(45) Date of Patent: Mar. 2, 2021

(54) PRESERVATION BOOSTER

(71) Applicant: DSM IP ASSETS B.V., Heerlen (NL)

(72) Inventor: Christine Mendrok-Edinger, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 107 days.

(21) Appl. No.: 16/208,616

(22) Filed: Dec. 4, 2018

(65) Prior Publication Data

US 2019/0167549 A1 Jun. 6, 2019

(30) Foreign Application Priority Data

Dec. 6, 2017 (EP) ..................................... 17205658

(51) Int. Cl.
| | | |
|---|---|---|
| *A61K 8/34* | (2006.01) | |
| *A61K 8/60* | (2006.01) | |
| *A61K 8/06* | (2006.01) | |
| *A61K 8/04* | (2006.01) | |
| *A61Q 5/02* | (2006.01) | |
| *A61Q 5/12* | (2006.01) | |
| *A61Q 19/00* | (2006.01) | |
| *A61K 31/121* | (2006.01) | |
| *A61K 31/047* | (2006.01) | |
| *A61K 47/10* | (2017.01) | |
| *A61K 47/26* | (2006.01) | |
| *A61K 9/00* | (2006.01) | |

(52) U.S. Cl.
CPC .............. *A61K 8/345* (2013.01); *A61K 8/042* (2013.01); *A61K 8/062* (2013.01); *A61K 8/064* (2013.01); *A61K 8/60* (2013.01); *A61K 9/0014* (2013.01); *A61K 31/047* (2013.01); *A61K 31/121* (2013.01); *A61K 47/10* (2013.01); *A61K 47/26* (2013.01); *A61Q 5/02* (2013.01); *A61Q 5/12* (2013.01); *A61Q 19/00* (2013.01); *A61K 2800/524* (2013.01); *A61K 2800/592* (2013.01); *A61K 2800/74* (2013.01)

(58) Field of Classification Search
None
See application file for complete search history.

(56) References Cited

U.S. PATENT DOCUMENTS

2014/0335029 A1\* 11/2014 Rudolph ............... C07C 67/303
424/55

\* cited by examiner

*Primary Examiner* — Nannette Holloman
(74) *Attorney, Agent, or Firm* — Nixon & Vanderhye P.C.

(57) ABSTRACT

The present invention relates to topical compositions comprising phytantriol and erythrulose as well as the use thereof for preservation boosting.

17 Claims, No Drawings

PRESERVATION BOOSTER

This application claims priority to EP Patent Application No. 17205658.2 filed Dec. 6, 2017, the entire contents of which are hereby incorporated by reference.

The present invention relates to topical compositions comprising phytantriol and erythrulose as well as the use thereof for preservation boosting.

Cosmetic compositions are particular susceptible to microbial contamination as they provide an excellent living environment for microorganisms. Thus, preservation and microbiological stability is an integral part of cosmetic formulation concepts in order to ensure product safety and compliance with legislation. However, demands such as global approval and soft preservation are limiting the number of acceptable actives. Increasing marketing pressure has resulted in an interest in reducing the amount of traditional preservatives in cosmetic formulations or in finding novel and mild ways to keep cosmetic products microbiologically stable. Therefore, concepts such as preservation boosting by ingredients generally accepted as safe become more and more important.

Thus, there is an ongoing need for finding synergistic combinations of active ingredients which are highly specific as well as effective against certain bacteria and thus offer mild preservation while enabling the production of dermatologically well accepted cosmetics and to balance the skin microbiome.

Erythrulose, is a well-accepted cosmetic ingredient which is often used in combination with dihydroxyacetone (DHA) in self-tanning cosmetics.

Phytantriol or 3,7,11,15-tetramethyl-1,2,3-hexadecanetriol (CAS number 74563-64-7) is a known compound. It has been used in cosmetic compositions, especially in combination with farnesol and at least one other active agent to regulate visible discontinuities or tactile skin (WO-2000/062745). It has also been described in EP-A-1161938 as an agent capable of limiting the penetration in the skin of pollutants, thus protecting against the deleterious effects of pollution.

Surprisingly it has now been found that a combination of phytantriol and erythrulose synergistically reduce the growth of *Escherichia coli* (*E. coli*) and can thus be used to protect cosmetic and/or pharmaceutical formulations against contamination with these bacteria. Due to its selectivity, the combination can furthermore be used for maintaining skin homeostasis and/or skin microbiome balance of a person in need of a treatment of an *E. coli* overpopulation on the skin Thus, in a first embodiment the present invention relates to topical compositions comprising phytantriol and erythrulose.

The term "phytantriol" in the present invention refers to phytantriol, 3,7,11,15-tetramethyl-hexadecane-1,2,3-triol, or 3,7,11,15-tetramethyl-1,2,3-hexadecanetriol (CAS number 74563-64-7, EC/List no.: 277-923-2). Phytantriol is commercially available.

The term "erythrulose" in the present invention refers to erythrulose in D- or L-form or as the racemate. Preferably L (+) Erythrulose, i.e. 2-Butanone, 1,3,4-trihydroxy-, (3S)-[CAS-no. 533-50-6], EC/List no.: 610-990-1 is used. Erythrulose is e.g. commercially available at DSM Nutritional Products Ltd, Kaiseraugst.

In a particular advantageous embodiment, the present invention relates to topical composition preserved against *E. coli*.

In a further embodiment of the present invention the topical compositions preferably comprise phytantriol in an amount selected in the range of about 0.01 to 2.9 wt. %, more preferably in the range of about 0.01 to 2.5 wt.-% and most preferably in the range of 0.05 to 2.0 wt.-% or even more preferred in the range of 0.05 to 1.5 wt %, based on the total weight of the composition.

In a further embodiment of the present invention the topical compositions preferably comprise erythrulose in an amount selected in the range of about 0.005 to 2 wt. %, more preferably in the range of about 0.01 to 1 wt.-% and most preferably in the range of 0.025 to 0.5 wt.-%, based on the total weight of the composition.

Preferably, in all embodiments of the present invention, the ratio (w/w) of phytantriol and erythrulose is selected in the range of about 40:1 to 0.1:1, more advantageously in the range of about 15:1 to 0.5:1, even more advantageously in the range of about 10:1 to 0.5:1.

Particular preferred are topical compositions comprising erythrulose in an amount selected in the range of 0.05 to 0.2 wt.-% and phytantriol in an amount selected in the range of 0.1 to 2 wt.-%, based on the total weight of the topical composition.

To make use of the preservation boosting activity of the combination of phytantriol and erythrulose, it can be used in a multiplicity of formulations or applications, such as, for example, cosmetic or pharmaceutical compositions, medicinal products or household products.

In particular, the topical composition comprising phytantriol and erythrulose is a cosmetic or pharmaceutical composition, and preferably a cosmetic (non-therapeutic) composition.

In all embodiments of the present invention, the use is preferably cosmetic (non-therapeutic) such as for maintenance of skin homeostasis or for the preservation of the topical composition itself against contamination with *E. coli*.

In one embodiment, the topical compositions comprising phytantriol and erythrulose according to the present invention are applied to mammalian keratinous tissue such as in particular to human skin or the human scalp and hair.

The term "cosmetic composition" as used in the present application refers to cosmetic compositions as defined under the heading "Kosmetika" in Römpp Lexikon Chemie, 10th edition 1997, Georg Thieme Verlag Stuttgart, New York as well as to cosmetic compositions as disclosed in A. Domsch, "Cosmetic Compositions", Verlag für chemische Industrie (ed. H. Ziolkowsky), 4th edition, 1992.

In one embodiment, the topical composition comprising phytantriol and erythrulose is an O/W emulsion, a W/O emulsion, a gel, a shampoo preparation or a hair conditioner.

Descriptions of O/W emulsions, W/O emulsions, gels, shampoo preparations or hair conditioners are given below.

In another embodiment, the invention relates to the use of phytantriol and/or erythrulose as a preservation booster.

The term "preservation booster" relates to one or more ingredients with synergistic and/or efficacy-boosting performance in view of preservation. Due to this effect, a lower amount of traditional preservatives or other preservative boosters can be used, and some undesired preservatives may even be avoided.

In a further embodiment, the present invention relates to the use of the topical composition comprising phytantriol and erythrulose for maintaining a healthy skin homeostasis and/or for maintaining skin microbiome balance.

Due to the mild but effective preservation against selective bacteria, the topical compostions are particularly suitable to maintain the skin homeostasis and the skin microbiome balance of persons in need of a treatment against an overpopulation of *E. coli*.

In another embodiment, the invention relates to the use of a combination of phytantriol and erythrulose as antimicrobial agent, in particular against *E. coli*.

The term "antimicrobial activity" (or "antimicrobial effect") as used herein means a capability of killing and/or inhibiting the growth of pathogenic or unwanted bacteria, such as in particular *Escherichia coli* (*Escherichia coli* ATCC 8739). The applied measuring method is NF EN ISO11930.

It is well understood, that the antimicrobial activity in the methods and uses according to the present invention is preferably non-medical, i.e. practiced in-vitro, ex-vivo respectively in cosmetic applications.

Due to the antimicrobial activity against transient and often pathogenic bacteria, such as in particular *E. coli*, the combination of phytantriol and erythrulose is further suitable for the treatment of adverse skin conditions associated with an overpopulation of *E. coli*. On the other hand, the selectivity of the combination allows that skin homeostasis and/or the balance of the skin microbiome is maintained.

In a further embodiment, the invention relates to a method for killing and/or inhibiting pathogenic bacteria, in particular *E. coli*, said method comprising contacting said pathogenic bacteria, in particular *E. coli*, with a combination of phytantriol and erythrulose.

In a further embodiment, the invention relates to a method of treating the skin and/or the scalp, said method comprising the steps of contacting the skin and/or scalp with a topical composition comprising phytantriol and erythrulose according to anyone of the embodiments as given herein.

In a further embodiment, the invention relates to a method of treating the skin and/or the scalp, said method comprising the steps of contacting the skin and/or scalp with the inventive topical composition comprising phytantriol and erythrulose for maintaining a healthy skin homeostasis and/or for maintaining skin microbiome balance.

The cosmetic or pharmaceutical compositions according to the present invention preferably further comprise a physiologically acceptable medium, that is to say a medium compatible with keratinous substances, such as the skin, mucosa, and keratinous fibers. Preferably, the physiologically acceptable medium is a cosmetically or pharmaceutically acceptable carrier.

The term cosmetically or pharmaceutically acceptable carrier refers to all carriers and/or excipients and/or diluents conventionally used in cosmetic compositions.

The topical compositions according to the present invention are generally prepared by admixing phytantriol and erythrulose in the amounts indicated herein with a suitable carrier.

The exact amount of carrier will depend upon the actual level of phytantriol and erythrulose and any other optional ingredients that one of ordinary skill in the art would classify as distinct from the carrier (e.g., other active ingredients).

In an advantageous embodiment, the cosmetic or pharmaceutical compositions according to the present invention comprise from about 50% to about 99%, preferably from about 60% to about 98%, more preferably from about 70% to about 98%, such as in particular from about 80% to about 95% of a carrier, based on the total weight of the cosmetic composition.

In a particular advantageous embodiment, the carrier consists furthermore of at least 40 wt.-%, more preferably of at least 50 wt.-%, most preferably of at least 55 wt.-% of water, such as in particular of about 55 to about 90 wt.-% of water.

The compositions of the invention (including the carrier) may comprise conventional adjuvants and additives, such as preservatives/antioxidants, fatty substances/oils, organic solvents, silicones, thickeners, softeners, emulsifiers, antifoaming agents, aesthetic components such as fragrances, surfactants, fillers, anionic, cationic, nonionic or amphoteric polymers or mixtures thereof, propellants, acidifying or basifying agents, dyes, colorings/colorants, abrasives, absorbents, chelating agents and/or sequestering agents, essential oils, skin sensates, astringents, pigments or any other ingredients usually formulated into such compositions.

In accordance with the present invention, the compositions according to the invention may also comprise further cosmetically active ingredients conventionally used in cosmetic or pharmaceutical compositions. Exemplary active ingredients encompass UV-filters, agents for the prevention or reduction of inflammation; firming, moisturizing, soothing, and/or energizing agents as well as agents to improve elasticity and skin barrier.

Examples of cosmetic excipients, diluents, adjuvants, additives as well as active ingredients commonly used in the skin care industry which are suitable for use in the cosmetic compositions of the present invention are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

The necessary amounts of the active ingredients as well as the excipients, diluents, adjuvants, additives etc. can, based on the desired product form and application, easily be determined by the skilled person. The additional ingredients can either be added to the oily phase, the aqueous phase or separately as deemed appropriate.

The cosmetically active ingredients useful herein can in some instances provide more than one benefit or operate via more than one mode of action.

Of course, one skilled in this art will take care to select the above mentioned optional additional ingredients, adjuvants, diluents and additives and/or their amounts such that the advantageous properties intrinsically associated with the combination in accordance with the invention are not, or not substantially, detrimentally affected by the envisaged addition or additions.

Preferably, the cosmetic or pharmaceutical compositions according to the invention are in the form of a suspension or dispersion in solvents or fatty substances, or alternatively in the form of an emulsion or micro emulsion (in particular of O/W- or W/O-type), PIT-emulsion, nano emulsion, multiple emulsion (e. g. O/W/O- or W/O/W-type), pickering emulsion, hydrogel, lipogel, one- or multiphase solution or vesicular dispersion.

The cosmetic or pharmaceutical compositions in accordance with the invention can be in the form of a liquid, lotion, a thickened lotion, a gel, a cream, a milk, an ointment or a paste.

The cosmetic or pharmaceutical compositions according to the invention have a pH in the range of 3-10, preferably in the range of pH of 3-8, most preferred in the range of pH 3-7.5. The pH is adjusted by methods known to a person skilled in the art, e.g. by using an acid such as a hydroxy acid including glycolic acid, lactic acid, malic acid, citric acid and tartaric acid or a base such as e.g. sodium or potassium hydroxide or ammonium hydroxide or amines such as triethanolamine or tromethamine as well as mixtures thereof.

Preferably, in the compositions according to the invention contain citric acid in an amount of at least 0.0001 wt.-%, such as e.g. in an amount of 0.01-1 wt.-%, in particular in an amount of 0.01 to 0.5 wt.-% is used for pH adjustment.

The cosmetic compositions according to the present invention advantageously comprise further preservatives or preservative booster. Preferably, the additional preservatives respectively preservative booster is selected from the group consisting of phenoxyethanol, ethylhexylglycerin, hydroxyacetophenone, glyceryl caprylate, caprylyl glycol, 1,2-hexanediol, propanediol, propylene glycol as well as mixtures thereof. When present, the preservative respectively preservative booster is preferably used in an amount of 0.01 to 2 wt.-%, more preferably in an amount of 0.05 to 1.5 wt.-%, most preferably in an amount of 0.1 to 1.0 wt.-%, based on the total weight of the composition. It is particularly preferred, that the cosmetic compositions according to the invention does not contain any further/other preservatives such as e.g. parabens and/or methylisothiazolidine.

The cosmetic compositions according to the present invention are in particular skin care preparations, functional preparations and/or hair care preparations such as most in particularly skin or hair care preparations.

Examples of skin care preparations are, in particular, light protective preparations, anti-ageing preparations, preparations for the treatment of photo-ageing, body oils, body lotions, body gels, treatment creams, skin protection ointments, moisturizing preparations such as moisturizing gels or moisturizing sprays, face and/or body moisturizers, as well as skin lightening preparations.

Examples of functional preparations are cosmetic compositions containing active ingredients such as hormone preparations, vitamin preparations, vegetable extract preparations, anti-ageing preparations, sunscreen preparations and/or antimicrobial (antibacterial or antifungal) preparations without being limited thereto.

In one embodiment, the cosmetic compositions according to the present invention are O/W emulsions, W/O emulsions and/or gels such as shower gels or hair gels.

The O/W emulsions according to the present invention advantageously comprise (i) phytantriol in an amount selected in the range of about 0.01 to 2.9 wt. %, more preferably in the range of about 0.01 to 2.5 wt.-% and most preferably in the range of 0.05 to 2.0 wt.-%, based on the total weight of the composition, (ii) erythrulose in an amount selected in the range of about 0.005 to 2 wt. %, more preferably in the range of about 0.01 to 1 wt.-% and most preferably in the range of 0.025 to 0.5 wt.-%, based on the total weight of the composition, (iii) water and (iv) at least one O/W- or Si/W-emulsifier selected from the list of glycerylstearatcitrate, glycerylstearate (self emulsifying), stearic acid, salts of stearic acid, polyglyceryl-3-methylglycosedistearate, ceteareth-20, steareth-2, steareth-12, PEG-40 stearate, phosphate esters and the salts thereof such as cetyl phosphate (Amphisol® A), diethanolamine cetyl phosphate (Amphisol® DEA), potassium cetyl phosphate (Amphisol® K), sodiumcetearylsulfat, sodium glyceryl oleate phosphate, hydrogenated vegetable glycerides phosphate, sorbitan oleate, sorbitan sesquioleate, sorbitan isostearate, sorbitan trioleate, lauryl glucoside, decyl glucoside, sodium stearoyl glutamate, sucrose polystearate and Hydrated Polyisobuten as well as mixtures thereof. Also, one or more synthetic polymers may be used as an emulsifier such as for example, PVP eicosene copolymer, acrylates/C10-3o alkyl acrylate crosspolymer, acrylates/steareth-20 methacrylate copolymer, PEG-22/dodecyl glycol copolymer, PEG-45/dodecyl glycol copolymer, and mixtures thereof. In a particular preferred embodiment the O/W-emulsifier is selected from the group of cetyl phosphates such as in particular potassium cetyl phosphate (commercially available as Amphisol® K), glyceryl stearate (and) PEG 100 stearate (commercially available as Arlacel® 165) and/or polyalkylenglycolether such as in particular laureth-35 (lauryl alcohol with 35 EO units; commercially available as Brij® 35). The at least one O/W emulsifier is preferably used in an amount of about 0.001 to 10 wt.-%, more preferably in an amount of 0.1 to 7 wt.-% with respect to the total weigh of the composition. Additionally, the cosmetic composition in the form of a O/W emulsion contains advantageously at least one co-emulsifier selected from the list of alkyl alcohols such as Cetyl Alcohol (Lorol C16, Lanette 16) Cetearyl Alcohol (Lanette® 0), Stearyl Alcohol (Lanette® 18), Behenyl Alcohol (Lanette® 22), Glyceryl Monostearate, Glyceryl Myristate (Estol® 3650), Hydrogenated Coco-Glycerides (Lipocire Na10) without being limited to this and mixtures thereof.

The W/O emulsions according to the present invention advantageously comprise (i) phytantriol in an amount selected in the range of about 0.01 to 2.9 wt. %, more preferably in the range of about 0.01 to 2.5 wt.-% and most preferably in the range of 0.05 to 2.0 wt.-%, based on the total weight of the composition, (ii) erythrulose in an amount selected in the range of about 0.005 to 2 wt. %, more preferably in the range of about 0.01 to 1 wt.-% and most preferably in the range of 0.025 to 0.5 wt.-%, based on the total weight of the composition, (iii) water and (iv) at least one W/O- or W/Si-emulsifier selected from the list of polyglyceryl-2-dipolyhydroxystearat, PEG-30 dipolyhydroxystearat, cetyl dimethicone copolyol, polyglyceryl-3 diisostearate polyglycerol esters of oleic/isostearic acid, polyglyceryl-6 hexaricinolate, polyglyceryl-4-oleate, polygylceryl-4 oleate/PEG-8 propylene glycol cocoate, magnesium stearate, sodium stearate, potassium laurate, potassium ricinoleate, sodium cocoate, sodium tallowate, potassium castorate, sodium oleate, and mixtures thereof. Further suitable W/Si-emulsifiers are Lauryl Polyglyceryl-3 Polydimethylsiloxyethyl Dimethicone and/or PEG-9 Polydimethylsiloxyethyl Dimethicone and/or Cetyl PEG/ PPG-10/1 Dimethicone and/or PEG-12 Dimethicone Crosspolymer and/or PEG/PPG-18/18 Dimethicone. The at least one W/O emulsifier is preferably used in an amount of about 0.001 to 10 wt.-%, more preferably in an amount of 0.2 to 7 wt.-% with respect to the total weigh of the composition.

The gel preparations according to the present invention advantageously comprise (i) phytantriol in an amount selected in the range of about 0.01 to 2.9 wt. %, more preferably in the range of about 0.01 to 2.5 wt.-% and most preferably in the range of 0.05 to 2.0 wt.-%, based on the total weight of the composition, (ii) erythrulose in an amount selected in the range of about 0.005 to 2 wt. %, more preferably in the range of about 0.01 to 1 wt.-% and most preferably in the range of 0.025 to 0.5 wt.-%, based on the total weight of the composition, (iii) water and (iv) at least one water soluble thickener. Such water-soluble thickeners are well known to a person skilled in the art and are e.g. listed in the "Handbook of Water soluble gums and resins" by Robert L. Davidson (Mc Graw Hill Book Company (1980)). Particularly suitable water soluble thickeners are selected from the group consisting of polyacrylic acids (e.g. commercially available under the tradename Carbomer or Carbopol®), homopolymers of 2-Acrylamido-2-methylpropansulfonic acid (e.g. commercially available as Rheothik®11-80), acrylate copolymers (e.g. commercially available under the tradename Pemulen® or Aculyn® 33), branched Poly(methacryloyloxyethyltrimethylammoniumchlorid) (INCI-name Polyquaternium-37), non-modified guar gums (e.g. commercially available under the tradename Jaguar), starch or derivatives thereof and/or hydroxyalkylcellulosen. Preferably the water-soluble thickener is used in an amount of about 0.001 to 10 wt.-%, more preferably in an amount of 0.2 to 7 wt.-%, based on the total weigh of the composition.

Examples of hair care preparations which are suitable according to the invention and which may be mentioned are shampoos, hair conditioners (also referred to as hair rinses), hairdressing compositions, hair tonics, hair regenerating compositions, hair lotions, water wave lotions, hair sprays, hair creams, hair gels, hair oils, hair pomades or hair brilliantines. Accordingly, these are always preparations which are applied to the hair and the scalp for a shorter or longer time depending on the actual purpose for which they are used.

If the hair care preparations according to the invention are supplied as shampoos, these can be clear liquids, opaque liquids (with pearly luster effect), in cream form, gel-like or else in powder form or in tablet form, and as aerosols. The surfactant raw materials on which these shampoos are based can be anionic, cationic, nonionic and amphoteric in nature and also be present in combinations of these substances.

Examples of anionic surfactants suitable for the incorporation into the shampoo preparations according to the present invention are $C_{10-20}$ alkyl- and alkylenecarboxylates, alkyl ether carboxylates, fatty alcohol sulfates, fatty alcohol ether sulfates, alkylolamide sulfates and sulfonates, fatty acid alkylolamide polyglycol ether sulfates, alkanesulfonates and hydroxyalkanesulfonates, olefinsulfonates, acyl esters of isothionates, alpha-sulfo fatty acid esters, alkylbenzenesulfonates, alkylphenol glycol ether sulfonates, sulfosuccinates, sulfosuccinic monoesters and diesters, fatty alcohol ether phosphates, protein-fatty acid condensation products, alkyl monoglyceride sulfates and sulfonates, alkyl glyceride ether sulfonates, fatty acid methyltaurides, fatty acid sarcosinates, and sulforicinoleates. These compounds and their mixtures are used in the form of their salts which are soluble in water or dispersible in water, for example the sodium, potassium, magnesium, ammonium, mono-, di- and triethanolammonium and analogous alkylanunonium salts.

Examples of suitable cationic surfactants are quaternary ammonium salts such as di($C_{10}$-$C_{24}$alkyl)dimethylammonium chloride or bromide, preferably di ($C_{12}$-$C_{18}$alkyl)-dimethylammonium chloride or bromide; $C_{10}$-$C_{24}$-alkyldimethylethylammonium chloride or bromide; $C_{10}$-$C_{24}$-alkyltrimethylammonium chloride or bromide, preferably cetyltrimethylammonium chloride or bromide and $C_{20}$-$C_{24}$-alkyltrimethylammonium chloride or bromide; $C_{10}$-$C_{24}$4-alkyldimethylbenzylammonium chloride or bromide, preferably $C_{12}$-$C_{18}$-alkyldimethylbenzylammoniumchloride; N—($C_{12}$-$C_{18}$-alkyl)pyridinium chloride or bromide, preferably N—($C_{12}$-$C_{16}$-alkyl) pyridinium chloride or bromide; N—($C_{12}$-$C_{18}$-alkyl)isoquinolinium chloride, bromide or monoalkyl sulfate; N—($C_{12}$-$C_{18}$-alkyloylcolaminoformylmethyl)pyridinium chloride; N—($C_{12}$-$C_{18}$-alkyl)-N-methylmorpholinium chloride, bromide or monoalkyl sulfate; N—($C_{12}$-$C_{18}$-alkyl)-N-ethylmorpholinium chloride, bromide or monoalkyl sulfate; $C_{16}$-$C_{18}$-alkylpentaoxethylammonium chloride; isobutylphenoxyethoxyethyldimethylbenzylammonium chloride; salts of N,N-diethylaminoethylstearylamide and oleylamide with hydrochloric acid, acetic acid, lactic acid, citric acid, phosphoric acid; N-acylamidoethyl-N,N-diethyl-N-methylammonium chloride, bromide or monoalkylsulfate and N-acylaminoethyl-N,N-diethyl-N-benzylammonium chloride, bromide or monoalkyl sulfate, where acyl is preferably stearyl or oleyl.

Examples of suitable nonionic surfactants which can be used as detergent substances are fatty alcohol ethoxylates (alkylpolyethylene glycols); alkylphenol polyethylene glycols; alkyl mercaptan polyethylene glycols; fattyamine ethoxylates (alkylaminopolyethylene glycols); fatty acid ethoxylates (acylpolyethylene glycols); polypropylene glycol ethoxylates (Pluronic); fatty acid alkylolamides (fatty acid amide polyethylene glycols); sucrose esters; sorbitol esters and polyglycol ether.

Examples of amphoteric surfactants which can be added to the shampoos are N—($C_{12}$-$C_{18}$-alkyl)-.beta.-aminopropionates and N—($C_{12}$-$C_{18}$-alkyl)-.beta.-iminodipropionates as alkali metal and mono-, di- and trialkylammonium salts; N-acylamidoalkyl-N,N-dimethylacetobetaine, preferably N—($C_8$-$C_{18}$-acyl)amidopropyl-N, N-dimethylacetobetaine; $C_{12}$-$C_{18}$-alkyldimethylsulfopropylbetaine; amphoteric surfactants based on imidazoline (commercial name: Miranol®, Steinapon®), preferably the sodium salt of 1-(β-carboxymethyloxyethyl)-1-(carboxymethyl)-2-laurylimidazolinium; amine oxide, for example $C_{12}$-$C_{18}$-alkyldimethylamine oxide, fatty acid amidoalkyldimethylamine oxide.

The hair care preparations according to the invention can additionally contain further additives customary in hair care such as for example perfumes, colorants, also those which simultaneously dye or tint the hair, solvents, opacifying agents and pearly luster agents, for example esters of fatty acids with polyols, magnesium and zinc salts of fatty acids, dispersions based on copolymers, thickening agents such as sodium, potassium and ammonium chloride, sodium sulfate, fatty acid alkylolamides, cellulose derivatives, natural rubbers, also plant extracts, protein derivatives such as gelatin, collagen hydrolysates, polypeptides with a natural or synthetic basis, egg yolk, lecithin, lanolin and lanolin derivatives, fats, oils, fatty alcohols, silicones, deodorizing agents, substances with antimicrobial activity, substances with anti-seborrhoeic activity, substances with keratolytic and keratoplastic effect, such as, for example, sulfur, salicylic acid and enzymes as well as further anti-dandruff agents such as olamine, climbazol, zink pyrithion, ketoconazole, salicylic acid, sulfur, tar preparations, derivatives of undecenic acid, extracts of nettel, rosmary, cottonwood, birch, walnut, willow bark and/or *arnica*.

The shampoos are produced in a manner known per se by mixing the individual components and where necessary further processing appropriate for the particular type of preparation.

Examples of hair care preparations in which the combination of phytantriol and erythrulose can be used according to the invention and which may be mentioned are hair conditioners, hair tonics and hair regenerating compositions, which are rinsed off from the hair after a certain time or, depending on the formulation, can also remain on the hair.

All these preparations are also produced as already mentioned for the shampoo in a manner known per se with the addition of the combination of phytantriol and erythrulose.

Particular suitable hair care preparations according to the present invention are shampoo preparations comprising (i) phytantriol in an amount selected in the range of about 0.01 to 2.9 wt. %, more preferably in the range of about 0.01 to 2.5 wt.-% and most preferably in the range of 0.05 to 2.0 wt.-%, based on the total weight of the composition, (ii) erythrulose in an amount selected in the range of about 0.005 to 2 wt. %, more preferably in the range of about 0.01 to 1 wt.-% and most preferably in the range of 0.025 to 0.5 wt.-%, based on the total weight of the composition, (iii) water and (vi) at least one anionic surfactant. Preferably, the anionic surfactant is selected from the group consisting of sodium lauryl sulfate, ammonium lauryl sulfate, sodium lauryl ether sulfate, ammonium lauryl ether sulfate, sodium lauroyl sarconisate, sodium oleylsuccinate, ammonium lauryl sulfosuccinate, sodium dodecylbenzol sulfonate and/or triethanolamine dodecylbenzol sulfonate or mixtures thereof, such as in particular sodium lauryl sulfate, ammonium lauryl sulfate, sodium lauryl ether sulfate and/or ammonium lauryl ether sulfate. The total amount of the anionic surfactant in the compositions according to the invention ranges from 0.5 to 45 wt.-%, preferably from 1.5 to 35 wt.-%, more preferably from 7 to 25 wt.-%, in particular from 7 to 15 wt.-% based on the total weight of the composition.

Particular suitable hair conditioners according to the present invention may be rinse off or leave on conditioners, preferably rinse-off conditioners. Particular advantageous hair conditioners according to the present invention comprise (i) phytantriol in an amount selected in the range of about 0.01 to 2.9 wt. %, more preferably in the range of about 0.01 to 2.5 wt.-% and most preferably in the range of 0.05 to 2.0 wt.-%, based on the total weight of the composition, (ii) erythrulose in an amount selected in the range of about 0.005 to 2 wt. %, more preferably in the range of about 0.01 to 1 wt.-% and most preferably in the range of 0.025 to 0.5 wt.-%, based on the total weight of the composition, (iii) water and (iv) at least one conditioning agent such as e.g. silicone oils, quaternary polymers, naturally derived conditioning agents without being limited thereto.

The quaternary polymer is preferably selected from e.g. Polyquaternium-6 (e.g. commercialized under the trade name TILAMAR® Quat 640 or 641), Polyquaternium-22 (e.g. commercialized under the trade name TILAMAR® Quat 2240 or 2241), Polyquaternium-7 (e.g. commercialized under the trade name TILAMAR® Quat 710, 711 or 712), etc, The naturally derived conditioning agents are preferably selected from e.g. sugar based polymers such as Guar Hydroxypropyltrimonium Chloride (e.g. commercialized under the trade name Jaguar C-17, Jaguar C-1000, Jaguar C-13S)), but not limited hereto. In principal, any silicone oil is suitable for use in the hair conditioner. However, the silicone oil is preferably selected from dimethicones, dimethiconols, polydimethylsiloxanes, arylated silicones, cyclic silicones, silicone surfactants and aminated silicones and may be volatile or non-volatile. Particular suitable silicone oils are dimethicone, dimethiconol, polydimethylsiloxane which are available from various suppliers such as Dow Corning. The total amount of the at least one silicone oil in the hair conditioner is preferably selected is in the range of 0.01 to 10 wt.-%, preferably 0.02 to 7.5 wt.-%, more preferably 0.05 to 5 wt.-% and most preferably 0.1 to 3 wt.-%, based on the total weight of the composition.

The following examples are provided to further illustrate the compositions and effects of the present invention. These examples are illustrative only and are not intended to limit the scope of the invention in any way.

EXAMPLE

The antimicrobial efficacy is assessed in analogy to the regulatory challenge test method (NF EN ISO11930). Thus, solutions of the respective active(s) in ethanol are prepared and further dissolved in physiological serum with 0.85 wt.-% NaCl in the concentrations as outlined in table 1 under sterile conditions. Samples containing phytantriol were solubilized in physiological serum supplemented with 10 wt.-% ethanol, samples containing erythrulose only were solubilized in physiological serum supplemented with 1 wt.-% ethanol.

The solutions of the active(s) were deposed in 96-deep well plates (1.6 ml/well). The wells are contaminated with the *Escherichia coli* at $1.5*10^5$ to $1*10^6$ cfu/ml to obtain the initial contamination as outlined in table 1. After the contamination, each well was thoroughly mixed to ensure a homogeneous distribution of *E. coli*. Then each plate was incubated at 22° C. for 24 h. The counting of the (remaining) population is carried out 24 h after contamination.

TABLE 1

Results

| Test solution | Time [h] | *Escherichia coli* colony count [cfu/ml] | Log reduction |
|---|---|---|---|
| 0.2 wt.-% phytantriol | 0 | 580000 | |
| | 24 | 1000 | −2.763 |
| 0.2 wt.-% erythrulose | 0 | 580000 | |
| | 24 | 33700 | −1.236 |
| 0.1 wt.-% phytantriol | 0 | 580000 | |
| 0.1 wt.-% erythrulose | 24 | 0 | −5.763 |

As can be seen in the table above the combination of phytantriol and erythrulose shows a synergistic effect against *E. coli* and can be used as preservation booster for cosmetic formulations (creams, gels, lotions, shampoos, conditioners, etc.) as well as to balance the population of *E. coli* on the skin.

The invention claimed is:

1. A method for killing and/or inhibiting *E. coli*, the method comprising contacting an area affected by *E. coli* with an effective *E. coli* killing and/or inhibiting amount of a composition comprising a combination of phytantriol and erythrulose.

2. The method according to claim 1, wherein the phytantriol is present in an amount of about 0.01 to 2.9 wt. %, based on the total weight of the composition.

3. The method according to claim 1, wherein the phytantriol is present in an amount of about 0.01 to 2.5 wt. %, based on the total weight of the composition.

4. The method according to claim 1, wherein the phytantriol is present in an amount of about 0.05 to 2.0 wt. %, based on the total weight of the composition.

5. The method according to claim 1, wherein the erythrulose is present in the composition in an amount of 0.005 to 2 wt. %, based on the total weight of the composition.

6. The method according to claim 1, wherein the erythrulose is present in the composition in an amount of 0.01 to 1 wt. %, based on the total weight of the composition.

7. The method according to claim 1, wherein the erythrulose is present in the composition in an amount of 0.025 to 1.5 wt. %, based on the total weight of the composition.

8. The method according to claim 1, wherein the erythrulose is present in the composition in an amount of 0.05 to 0.2 wt. % and the phytantriol is present in the composition in an amount of 0.1 to 2 wt. %, based on the total weight of the composition.

9. The method according to claim 1, wherein the phytantriol and the erythrulose are present in the composition in a ratio (w/w) of the phytantriol to the erythrulose of 40:1 to 0.1:1.

10. The method according to claim 9, wherein the ratio (w/w) of the phytantriol to the erythrulose is 15:1 to 0.5:1.

11. The method according to claim 9, wherein the ratio (w/w) of the phytantriol to the erythrulose is 10:1 to 0.5:1.

12. The method according to claim 1, wherein the composition is a cosmetic or pharmaceutical composition.

13. The method according to claim 1, wherein the composition has a pH of 3-10.

14. The method according to claim 13, further comprising an amount of 0.01 to 1 wt. %, based on the total weight of the composition, of citric acid as a pH adjuster.

15. The method according to claim 1, wherein the composition further comprises 0.01 to 2 wt. %, based on the total weight of the composition, of a preservative selected from the group consisting of phenoxyethanol, ethylhexylglycerin, hydroxyacetophenone, glyceryl caprylate, caprylyl glycol, 1,2-hexanediol, propanediol, propylene glycol and mixtures thereof.

16. The method according to claim 1, wherein the composition is a shampoo preparation, a hair conditioner, an oil-in-water (O/W) emulsion, a water-in-oil (W/O) emulsion or a gel.

17. The method according to claim 16, wherein the composition further comprises water and at least one agent selected from the group consisting of surfactants, emulsifiers, thickeners and oils.

\* \* \* \* \*